(12) United States Patent
Aime et al.

(10) Patent No.: US 8,518,373 B2
(45) Date of Patent: Aug. 27, 2013

(54) IONIC AND NON-IONIC RADIOGRAPHIC CONTRAST AGENTS FOR USE IN COMBINED X-RAY AND NUCLEAR MAGNETIC RESONANCE DIAGNOSTICS

(75) Inventors: Silvio Aime, Turin (IT); Alessandro Barge, Turin (IT); Valentina Mainero, Ivrea (IT); Fulvio Uggeri, Lodi (IT); Dario Livio Longo, Turin (IT); Enzo Terreno, Turin (IT); Walter Dastrù, Turin (IT)

(73) Assignee: Bracco Imaging SpA, San Donato Milanese (MI) (IT)

( * ) Notice: Subject to any disclaimer, the term of this patent is extended or adjusted under 35 U.S.C. 154(b) by 435 days.

(21) Appl. No.: 12/635,161

(22) Filed: Dec. 10, 2009

(65) Prior Publication Data
US 2010/0135913 A1    Jun. 3, 2010

Related U.S. Application Data

(63) Continuation-in-part of application No. 10/485,878, filed as application No. PCT/EP02/08183 on Jul. 23, 2002, now Pat. No. 8,211,404.

(30) Foreign Application Priority Data

Aug. 3, 2001    (IT) ............................ MI2001A1706

(51) Int. Cl.
*A61B 5/055*    (2006.01)
(52) U.S. Cl.
CPC ...................................... *A61B 5/055* (2013.01)
USPC .......................................................... 424/9.3
(58) Field of Classification Search
CPC ....................................................... A61B 5/055
USPC ............................................................ 424/9.3
See application file for complete search history.

(56) References Cited

U.S. PATENT DOCUMENTS 5,648,536 A    7/1997 Dunn et al.
2005/0136002 A1*    6/2005 Fossheim et al. ............ 424/1.11

FOREIGN PATENT DOCUMENTS

EP              0 759 785          3/1997
WO        WO 00/75141          12/2000

OTHER PUBLICATIONS

Aime et al. (Mag. Res. Med. 2005, 53, 830-834).*
Ward et al. (Mag. Res. Med. 2000, 44, 799-802).*
Sun et al. (Mag. Res. Med. 2007, 58, 1207-1215).*
Mittal et al. (Neuroradiol. 1999, 41, 480-486).*
McKenzie et al. (J. Mag. Res. Imaging 2006, 24, 928-933).*
Stancanello et al. (Contrast Media Mol. Imag. 2008, 3, 136-149).*
PCT International Search Report for PCT/EP02/08183 dated Jan. 31, 2003.
PCT International Preliminary Examination Report for PCT/EP02/08183 dated Jan. 15, 2004.
Hergan et al.; "Effects of iodinated contrast agents in MR imaging", European Journal of Radiology, vol. 21, 1995, pp. 11-17.
Ward et al; "A new class of contrast agents for MRI based on proton chemical exchange dependent saturation transfer (CEST)", Journal of Magnetic Resonance, vol. 143, 2000, pp. 79-87.

* cited by examiner

*Primary Examiner* — Michael G Hartley
*Assistant Examiner* — Melissa Perreira
(74) *Attorney, Agent, or Firm* — Robert E. Alderson, Jr.

(57) ABSTRACT

The invention concerns a method for obtaining diagnostic images of a human or animal body organ, region, fluid or tissue by using combined X-ray and/or Magnetization Transfer (MT) based MRI techniques and iodinated radiographic compounds as contrast agents, as well as improved Chemical Exchange dependent Saturation Transfer (CESDT or CEST) based MRI procedures in which a iodinated contrast agents is used for in vivo determining a physiological parameter of diagnostic interest.

6 Claims, 10 Drawing Sheets

IONIC AND NON-IONIC RADIOGRAPHIC CONTRAST AGENTS FOR USE IN COMBINED X-RAY AND NUCLEAR MAGNETIC RESONANCE DIAGNOSTICS

CROSS-REFERENCE TO RELATED APPLICATIONS

This application is a continuation-in-part of U.S. patent application Ser. No. 10/485,878, filed Dec. 6, 2004, which is a national stage filing of corresponding international application number PCT/EP02/08183, filed Jul. 23, 2002, which claims priority of Italian Application No. MI2001A001706, filed Aug. 3, 2001, all of which are hereby incorporated by reference.

The present invention discloses the use of radiographic contrast agents for the preparation of diagnostic formulations for the sequential or simultaneous X-ray and nuclear magnetic resonance (MRI) diagnostics.

The invention further concerns a method for obtaining diagnostic images of a human or animal body organ, region, fluid or tissue by using combined X-ray and/or Magnetization Transfer (MT) based MRI techniques and iodinated radiographic compounds as contrast agents, as well as improved Chemical Exchange dependent Saturation Transfer (CESDT or CEST) based MRI procedures in which a iodinated contrast agents is used for in vivo determining a physiological parameter of diagnostic interest.

X-ray contrast agents used in in vivo diagnostics are usually characterized by high water solubility, low viscosity, low osmotic pressure, high contrast density, low toxicity and good tolerability.

The clinical use of non-ionic contrast agents has gradually replaced that of ionic contrast agents which, on the other hand, are still being used (see e.g. Renografin) in some diagnostic applications.

Examples of non-ionic contrastographic agents comprise Ioexol, Iomeprol, Iopentol, Iopromide, Ioversol, Ioxilan, Iodixanol and Iopamidol.

On the other side, conventional Magnetic Resonance Imaging diagnostic procedures mainly use paramagnetic compounds, preferably chelated complexes of bi- or trivalent paramagnetic metal ions with polyaminopolycarboxylic acids and/or their derivatives or analogues which act by affecting the relaxation times T1 and T2 of the bulk water protons through the exchange with water molecules in their coordination spheres (Caravan P, et al. Chem Rev 1999, 99:2293-2352; the Chemistry of Contrast Agents in Medical Magnetic Resonance Imaging. Chichester, UK: John Wiley & Sons; 2001. p 45-120). The effect they provide on both T1 and T2 is similar but, being T1 usually significantly longer than T2 in most biological tissues, they are more often exploited in T1-weighted imaging, to shorten T1 relaxation time of surrounding water protons, thus leading to an increased signal that results in brighter spots in the images. For this reason they are also called positive contrast agents.

Negative contrast agents, instead, are used to shorten T2, leading to a decreased signal (appearing dark on MRI) on T2-weighted images.

Currently available MRI contrast agents comprise paramagnetic complexes such as Gd-DTPA, MAGNEVIST®; Gd-ROTA, DOTAREM®; Gd-HPDO3A, PROHANCE®; Gd-DTPA-BMA, OMNISCAN®.

The contrast agents listed above are designed for a wholly general use. In fact, after intravenous administration, the MRI contrast agent is distributed in the extracellular spaces in different parts of the body prior to being excreted. In this sense they are similar to iodine compounds used in X ray medical diagnosis.

A recently proposed technique for MRI diagnostic is the magnetization transfer technique (see e.g. J. Chem. Phys. 39 (11), 2892-2901, 1963), in which the proton signal of a molecule, present in the medium or added thereto, is suitably irradiated with a radiofrequency signal generated by the apparatus magnetic field, and transferred through magnetization to the water molecules surrounding the compound, i.e. the so-called "bulk water" of the medium.

The parameters affecting this process are related to different factors such as the nature of the chemical group involved in the proton transfer, the pH of the solution, the temperature of the medium and the intensity of the applied magnetic field.

U.S. Pat. No. 5,050,609 discloses the use of the saturation transfer technique in magnetic resonance, which consists in the magnetization transfer in the presence of an irradiating field able to saturate the protons involved in the exchange process, which procedure is used in vitro and provides further information from the analyzed samples, e.g. biological tissues, polymeric compounds or samples of solid compounds of geologic interest.

The use of Magnetization Transfer in animal or patients that have been administered with Gd-based contrast agents to increase the conspicuousness of the Gd associated enhancement in conventional T1-weighted MR images by darkening the background tissue is disclosed in Radiology, 192, 593-599, 1994 and in Invest. Radiol. 33, 560-572, 1998.

Mag. Res. In Medicine, 44, 799-802, 2000, describes a procedure for the determination of the pH in solution using the magnetization signal transfer technique in MRI, in the presence of 5-hydroxy trypthophan or 5,6-dihydrouracil.

Investigative Radiology, 23, S267-270, 1988, describes the effect of some compounds such as arginine, glycine, Iopamidol, ornithine, serine and serinol, in conventional MRI, in inducing a contrast increase by decreasing T2 relaxation time, i.e. transversal relaxation time of water protons. The decrease of T2, which is experimentally observed, causes a decrease in the intensity of the resulting imaging signal, that is mainly ascribed to the chemical exchange between the mobile proton of the molecule and bulk water.

Furthermore, both J. of Mag. Res., 143, 79-87, 2000 and WO00/66180 disclose the use of some compounds in MRI with saturation transfer techniques of the proton signal. In particular, WO00/66180 discloses a method for enhancing the contrast of MRI images using Chemical Exchange dependent Saturation Transfer and provides contrast agents functioning for performing MRI-CEST analyses both in vivo and in vitro.

The compounds used for this purpose are all diamagnetic and belong to different chemical classes, consisting of sugars (e.g. mannitol, sorbitol, fructose, maltose, lactose and dextran), amino acids (e.g. L-Ala, L-Arg, L-Lys), nucleosides, purine and pyrimidine bases, barbituric acid, imidazole compounds and other heterocyclic compounds. A ratiometric method for the pH measurement which is independent on the contrast agent concentration is also disclosed.

However, when the former diamagnetic compounds are used in MT imaging, a significant ST effect is generally recovered under acidic conditions, wherein this render hardly exploitable their use in in vivo applications, i.e. under physiological, not acidic conditions.

A further limit of such diamagnetic agents is represented by their rather low sensitivity, which determines the need of using the highest possible doses thereof to generate a sufficiently large CEST effect. This, however, results in a high probability of toxic or physiological effect in vivo, and render Their clinical use in vivo troublesome, although their enteral toxicity is not particularly high (see, for instance, Merck Index 12$^{th}$ ed.: 972. Barbital LD orally in mice: 600 mg/Kg; 973. Barbituric Acid LD50 orally in male rats: >5000 mg/kg; 4475. Guanidine LD orally in rabbits: 500 mg/kg; RTECS Vol. 5 and. 1985-86: 82776. Thymidine LD50 intraperitoneal mouse 2512 mg/kg; 60194. Pipecolinic. Acid LD50 intravenous mouse 2200 mg/kg; 9721. L-Arginine LD50 intravenous mouse 2030 mg/kg; 41867. 2-Imidazolidinone LD50 intraperitoneal mouse 500 mg/kg; 41826. 2-Imidazolidinetione LD50 intraperitoneal mouse 200 mg/kg).

As a result, none of the diamagnetic contrast agents provided by the cited art is actually used in the current clinical practice.

DESCRIPTION OF THE INVENTION

Figure 1:
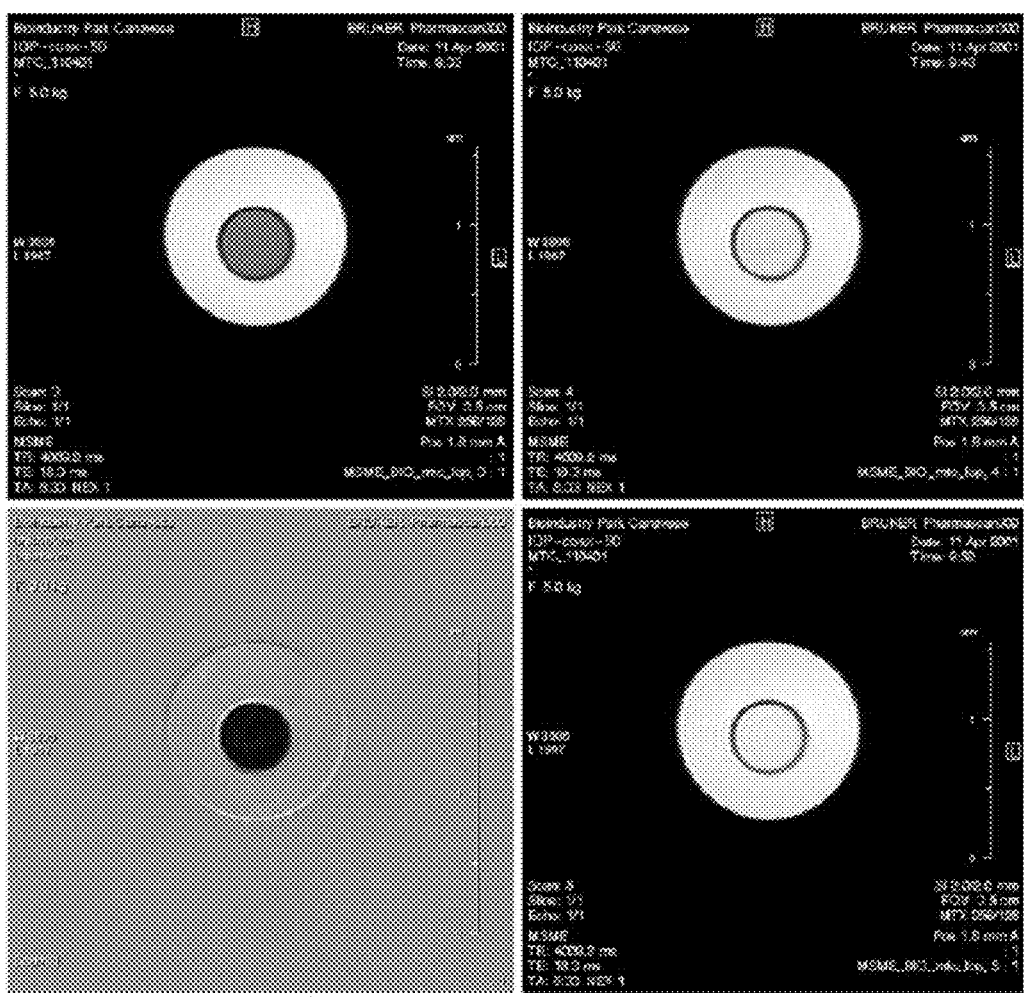
FIG. 1 reports images obtained in contrast ability tests (in vitro tests) using a 50 mM solution of Iopamidol.

Nowadays, one of the most pressing requests by the medical class concerns the availability of innovative contrast media able to conjugate high in vivo safety with improved effectiveness and consenting the diagnostic visualization of specific organs or disorders, which usually are not effectively evidenced with the known techniques.

X ray diagnostic contrast agents are an extremely versatile and interesting class of compounds widely used in clinics thanks to their effectiveness, low toxicity and safety of use in diagnosis concerning different districts of the human body, such as in urography, angiography, ventriculography and myelography.

The possibility of using the same contrast medium for both X ray radiology and MRI diagnostics would remarkably widen the diagnostic potentialities of the administered compound and provide diagnostic results so far unexpected.

Moreover, the availability of a single contrast agent providing diagnostic results through different techniques, which previously required the use of different contrast agents, is an important innovative aspect of the diagnostic technique, particularly in clinics, where diagnostic procedures based on both the usual radiographic procedures, computerized axial tomography (CAT) and magnetic resonance imaging are nowadays employed.

In addiction, in case of iodinated contrast agents, the use of a single compound for a number of diagnostic procedures would be advantageous also since the total amount of the administered product is by far higher than that of other medicaments.

By way of example, the dose of opacifying agent being injected can reach and even exceed 150 g and the combination of two diagnostic techniques would be cost-saving.

However, while the use of these agents in X ray diagnostic imaging is known for a long time, their use in MT based MRI imaging (or CEST based MRI imaging, as used herein interchangeably), and/or in the combined X-ray and MRI imaging has never been disclosed.

Therefore, a first object of the present invention is the use of a iodinated contrast agent comprising at least one amido function for the preparation of a diagnostic formulation to obtain in vitro or in vivo images using magnetization transfer MRI techniques, alone or combined with X-ray radiography.

A further object of the invention is a method for obtaining in vivo or in vitro (ex vivo), diagnostic images which comprises administering a diagnostic formulation including one or more iodinated contrast agents endowed with at least one amido function to an individual or to an organ, or other body region, fluid or tissue of the individual and recording contrasted images of the said individual, organ, body art or tissue by use of radiological and/or Magnetization Transfer MRI techniques.

"Iodinated contrast agents comprising at least one amido function" as used herein means iodinated aromatic compounds having a triiodinated aromatic ring bearing at the remaining positions straight or branched, functionally substituted organic residues or an organic compound comprising at least two triiodinated aromatic residues mutually covalently linked at one of the positions, either directly or through a straight or branched, functionally substituted organic residue, said aromatic ring being further substituted at the remaining positions by straight or branched, functionally substituted organic residues and in which the organic residues and the triiodinated aromatic ring are linked by amido functions.

Examples of contrast agents for use according to the invention comprise the compounds of general formula (I), (II), (III) and (IV) reported below, the corresponding isomers and stereoisomers, in particular the exo, endo regioisomers; the corresponding enantiomeric, racemic and meso forms as well as the salts thereof with physiologically compatible bases or acids.

"Individual" or "patient", as used herein interchangeably, means an animal, preferably a mammalian and, most preferably, a human subject, in need for the diagnostic visualization.

The method of the invention is based on the use of iodinated contrast agents having one or more mobile protons able to exchange with bulk water, i.e. the surrounding water molecules present in the medium and in the biological tissues. Preferably, the said mobile proton(s) belong to amido function(s) of the iodinated contrast agents.

Irradiation of the mobile proton(s) of the considered iodinated molecule with a radiofrequency field tuned on the resonance frequency of the concerned proton(s) induces saturation transfer (ST) to the bulk water signal, caused by the chemical exchange between the proton of the "exogen" molecule and water. As a result, the saturation of the water signal is obtained that appears as a decrease in the signal intensity in the MRI image obtained at the body site and/or on in vivo or in vitro (ex vivo) samples, involved in the saturation transfer.

In other words, the transfer of the saturation (or saturation transfer) from the irradiated (and thus saturated) mobile proton(s) of the administered contrast agent to the surrounding water protons causes a decrease in the resulting MRI water proton signal, which is the most important contribution to Magnetic Resonance images that are registered.

The greater is the amount of saturation transfer (and, therefore, the ST value) the lower is the resulting water proton signal and, therefore, the more marked is the contrast in the recorded MRI image.

Advantageously, according to the method of the instant invention a single dose of iodinated contrast agent is used, either in vivo or in vitro (ex vivo) for performing the radiological and/or MRI diagnostic analysis at different times and depending on the used technique, starting from one or the other diagnostic procedure.

Accordingly, in one embodiment the invention relates to a method of obtaining in vivo or in vitro, (ex vivo), images comprising the steps of:

(a) administering a diagnostic formulation comprising one or more iodinated contrast agents having mobile protons able to exchange with bulk water to an individual or to an organ or other body region, fluid or tissue of the individual, (b) imaging, with magnetization transfer based MRI techniques the said organ, body region, fluid or tissue of the individual to form an MRI image, and (c) recording contrasted images.

In the method of the invention, the resulting MRI images are suitably acquired before and/or after irradiation in the radiofrequency field of the proton that exchanges with the water of the medium. Moreover, optionally, the imaging with Magnetization Transfer techniques is carried out coupled with a radiographic imaging that can conveniently be carried out before or after MT based MRI investigation.

In this case, the results obtained from the whole investigation allows to compare images obtained with X rays and with MRI.

The sequence of the radiological and MRI techniques, which are considered complementary, can be reversed, depending on the body site concerned and the diagnostic analysis. In fact, it may be convenient to carry out first MRI on the body angiographic district, then a radiological urographic investigation.

A further object of the present invention is the use of the disclosed MT based diagnostic technique alone, using the above defined iodinated compounds as contrast agents.

In a preferred embodiment, the invention relates to a method of obtaining in vivo or in vitro, ex vivo, images comprising the steps of:

(a) administering a diagnostic formulation comprising one or more iodinated contrast agents having mobile protons able to exchange with bulk water to an individual or to an organ or other body region or tissue of the individual, (b') irradiating the mobile proton(s) of the administered agent with a radiofrequency field tuned on the resonance frequency of the concerned proton(s) thus inducing, through chemical exchange, saturation transfer to the bulk water signal, (b") determining the decrease in the water proton signal intensity is generated by the saturation transfer to form an MRI image of an organ or other body region, fluid or tissue of the individual, by using MT-based MRI techniques, and (c) recording the contrasted images.

The advantages deriving from the use of the above class of radiographic compounds according to the invention are mainly related to their provenlow in vivo toxicity, which makes them easy to use at different dosages, depending on the particular product used and on the concerned body site. Other advantageous aspects of these compounds are their high water solubility and chemical stability, and well-established pharmacokinetic (see e.g. RoFo Suppl. 128, 220-223 (1989); Invest. Radio., 18, 368-374, 1983; Invest. Radio., 26, S156-S158, 1991) in terms of transport rate in circulation or in other body cavities, retention time in the organs under examination, excretion and clearance.

A first preferred group of iodinated contrast agents comprising amido functions are the compounds of formula (I)

(I)

in which:

A, D, E, which can be the same or different, are groups of formula —CON(R)R$_1$, —COOH, —CONH$_2$ or —N(R)—COR$_2$ or CH$_2$N(R)—COR$_2$;

R is H or R$_1$, with the proviso that the substituent R is H in at least one group of the compound;

R$_1$ is a straight or branched (C$_1$-C$_6$) alkyl residue, optionally substituted with 1-5 hydroxy and/or alkoxy and/or hydroxy-alkoxy groups, or with a NH—CO—R$_1$ or —CO—N(R)R$_1$ group, or R$_1$ is a carbohydrate residue;

R$_2$ is a straight or branched (C$_1$-C$_6$) alkyl residue, optionally substituted with 1-5 hydroxy and/or alkoxy and/or hydroxyalkoxy groups and optionally interrupted by an oxo group.

A second preferred group of iodinated contrast agents comprising amido functions includes compounds of formula (II)

(II)

in which:

A, D and E are as defined above;

B and B', which can be the same or different, are a covalent bond or are selected from —CO—N(R)—, —N(R)—CO— or —N(COR$_3$)— groups, in which R is H or a residue of a straight or branched ($C_1$-$C_6$) alkyl group, optionally substituted with 1-5 hydroxy and/or alkoxy and/or hydroxyalkoxy groups; $R_3$ is a ($C_1$-$C_3$) alkyl residue, optionally substituted with 1-2 hydroxy or alkoxy or hydroxyalkoxy groups;

X is a covalent bond or a straight or branched ($C_1$-$C_8$) alkylene chain, optionally substituted with 1-6 hydroxy and/or —CO—NHR groups, and optionally interrupted by —O—, —S—, —N—, —N(R)—CO groups;

in case both groups B and X are absent, the two aromatic compounds are directly linked with a covalent bond with the proviso that the substituent R is H in at least one group of the compound.

Preferred compounds of general formula (I) are the compounds of general formula (III) in which:

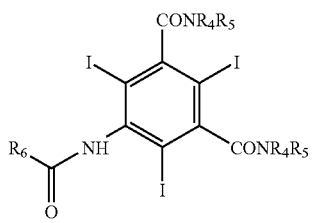
(III)

$R_4$, $R_5$, which can be the same or different, are H or a straight or branched ($C_1$-$C_3$) alkyl group, which can optionally be substituted with 1-2 hydroxy and/or alkoxy and/or hydroxyalkoxy groups;

$R_6$ is a straight or branched ($C_1$-$C_4$) alkyl group containing one or more hydroxy, alkoxy or acyloxy groups.

An example of particularly preferred compounds of general formula (I) and (III) are those compounds known under the names of Iopamidol and Iopromide (see scheme 1).

Scheme 1

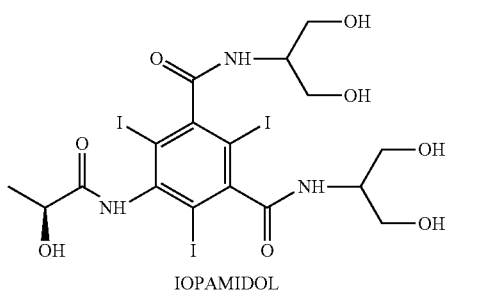

IOPAMIDOL

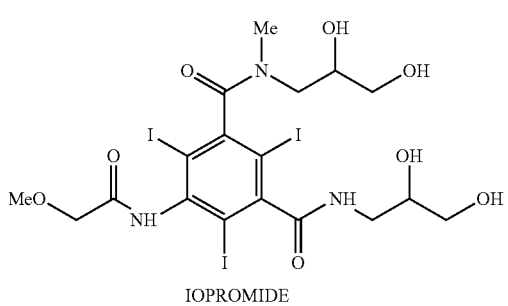

IOPROMIDE

A further preferred group of iodinated contrast agents comprising amido functions comprises compounds of formula (IV):

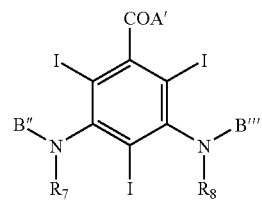
(IV)

in which:

A' is a OH or —$NHR_1$ group;

$R_1$ is a straight or branched ($C_1$-$C_6$) alkyl group, optionally substituted with 1-5 hydroxy and/or alkoxy and/or hydroxyalkoxy groups, or by a —NH—CO—$R_1$ or —CO—$NHR_1$ group, or $R_1$ is a carbohydrate residue;

B" and B'", which can be the same or different, are H or $R_1$, as defined above;

$R_7$ and $R_8$, which can be the same or different, are H, an acyl —$COR_1$ group, an alkyl group, a mono or polyhydroxyalkyl group or a carbohydrate residue;

with the proviso that at least one of the groups B", B'", $R_7$ or $R_8$ is H.

A particularly preferred example of the compounds of formula (IV) is the Metrizamide (see scheme 2 below U.S. Pat. No. 3,701,771 and U.S. Pat. No. 4,021,481), a water-soluble, non-ionic contrast agent having moderate toxicity and usually present as isomeric mixture.

A further preferred compound is diatrizoic acid (compound of formula IV), Renografin® (see scheme 2 and e.g. Radiology 140: 507-511, 1981; Biochimica et Biophysica Acta. 756, 106-110, 1983, Elsevier Biomedical Press and U.S. Pat. No. 4,192,859, U.S. Pat. No. 4,567,034 and U.S. Pat. No. 4,735,795) which is particularly suitable for the use according to the present invention.

Scheme 2

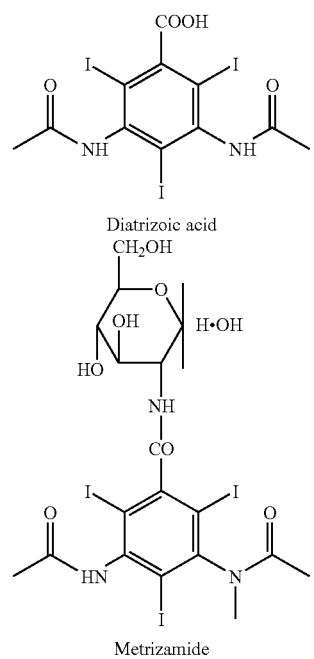

Examples of particularly preferred compounds of general formula (I) are the compounds reported in Scheme 3 below.

Scheme 3

| Non-proprietary name CAS [RN] | A | D | E |
|---|---|---|---|
| Metrizamide [31112-62-6] | —CONHCH(CHO)(CHOH)$_3$CH$_2$OH | —N(Me)Ac | —NH—Ac |
| Iopamidol [60166-93-0] | —CONHCH(CH$_2$OH)$_2$ | —CONHCH(CH$_2$OH)$_2$ | —NHCOCH(OH)CH$_3$ |
| Iopromide [73334-07-3] | —CONHCH(CH$_2$OH)$_2$ | —CON(Me)CH$_2$CH(OH)CH$_2$OH | —NHCOCH$_2$OMe |
| Iogulamide [75751-89-2] | —CONHCH$_2$CH(OH)CH$_2$OH | —CONHCH$_2$CH(OH)CH$_2$OH | —NHCOCO(CHOH)$_3$CH$_2$OH |
| Iodamide [440-58-4] | —COOH | —NHCOCH$_3$ | —CH$_2$NHCOCH$_3$ |
| Ioglucol [63941-73-1] | —CONHMe | —NHCO(CHOH)$_4$CH$_2$OH | —N(Ac)CH$_2$CH$_2$OH |
| Ioglucomide [63941-74-2] | —CONHMe | —NHCO(CHOH)$_4$CH$_2$OH | —NHCO(CHOH)$_4$CH$_2$OH |
| Ioglunide [56562-79-9] | —CONHCH$_2$CH$_2$OH | —NHCO(CHOH)$_4$CH$_2$OH | —N(Me)Ac |
| Iobitridol [136949-58-1] | —NHCOCH(CH$_2$OH)$_2$ | —CON(Me)CH$_2$CH(OH)CH$_2$OH | —CON(Me)CH$_2$CH(OH)CH$_2$OH |
| Iocibidol [79211-34-0] | —CON(Me)CH$_2$CH(OH)CH$_2$OH | —CONHCH$_2$CH(OH)CH$_2$OH | —CONH$_2$ |
| MP-10007 [77111-65-0] | —CONHCH$_2$CH$_2$OH | —NHCOCO(CHOH)$_3$CH$_2$OH | —NHCOCO(CHOH)$_3$CH$_2$OH |
| Iotriside [79211-34-0] | —CONH$_2$ | —CONHCH$_2$CH(OH)CH$_2$OH | —CON(Me)CH$_2$CH(OH)CH$_2$OH |
| Sodium diatrizoate [737-31-5] | —COONa | —NHCOCH$_3$ | —NHCOCH$_3$ |

Furthermore, the compounds of formula (II) reported in the following, Scheme 4 are particularly preferred.

Scheme 4

| Non-proprietary name CAS [RN] | A | D = E | B-X-B |
|---|---|---|---|
| Iofratol [141660-63-1] | —CONHCH(CH$_2$OH)$_2$ | —NHCOCH(OH)CH$_3$ | —CONHCH$_2$CH(OH)CH$_2$OH |
| Iotasul [71767-13-0] | —CON(Me)CH$_2$CH(OH)CH$_2$OH | —CON(Me)CH$_2$CH(OH)CH$_2$OH | —NHCOCH$_2$CH$_2$—S—CH$_2$CH$_2$CONH— |
| (WO 9208691) [143200-04-8] | —CONHCH$_2$CH(OH)CH$_2$OH | —NHCOCH$_2$OH | —CONHCH$_2$CH(OH)CH$_2$NHCO— |
| (WO 9208691) [143199-77-3] | —CONHCH(CH$_2$OH)$_2$ | —NHCOCH$_2$OH | —CONHCH$_2$CH(OH)CH$_2$NHCO— |
| (WO 9208691) [143200-00-4] | —CONHCH$_2$CH(OH)CH$_2$OH | —NHCOCH$_2$OH | —CONHCH$_2$C(CH$_2$OH)$_2$CH$_2$NHCO— |

Particularly preferred compounds for use according to the present invention comprise: Iopamidol, Iofratol, Iopromide, Metrizamide, Iogulamide, Ioglunide, Iobitridol, Iodamide, Sodium diatrizoate and other diatrizoic acid salts, and possible combinations thereof.

Other contrast agents for use according to the present invention are described in the following patents, herein incorporated by reference: U.S. Pat. No. 4,364,921, U.S. Pat. No. 4,284,620, U.S. Pat. No. 3,701,771, U.S. Pat. No. 4,001,323, U.S. Pat. No. 4,001,323, U.S. Pat. No. 4,250,113, U.S. Pat. No. 4,396,598, U.S. Pat. No. 4,192,859, U.S. Pat. No. 5,663,413, U.S. Pat. No. 4,239,747, U.S. Pat. No. 4,014,986, EP 108 638, WO 9208691, WO 9515307, EP 33 426, U.S. Pat. No.

4,567,034, U.S. Pat. No. 4,735,795, U.S. Pat. No. 5,869,024, U.S. Pat. No. 5,527,926, EP 431 838, EP 437 144.

Iopamidol is a particularly preferred iodinated agent.

The use of aqueous compositions of liposomes consisting of lipid molecules mono-, bi- or multi-layers as carriers for the compounds used as contrast agents is particularly preferred.

U.S. Pat. No. 4,192,859 discloses the preparation of liposomes made of lecithin and sterols, containing 20 to 60% by weight of contrast agent for use in imaging of organs, and in particular of endothelial reticule, cardiovascular system and also for lymphographies. Compounds that can be used for this purpose (U.S. Pat. No. 5,445,810) comprise, for example, the following contrast agents:

Iopamidol, metrizamide, diatrizoic acid, sodium diatrizoate, meglumine diatrizoate, acetrizoic acid and the soluble salts thereof, diprotizoic acid, Iodamide, Iodipamide sodium salt, Iodipamide meglumine salt, iodohippuric acid and the soluble salts thereof, iodometamic acid, iodopyracetiodo-2-pyridone-N-acetic acid, 3,5-diiodo-4-pyridone-N-acetic acid (Iodopiracet) and its diethyl ammonium salt, iothalamic acid, metrizoic acid and the salts thereof, ipanoic, iocetamic, iophenoxic acids and the soluble salts thereof, sodium tyropanoate, sodium hypodate and other similar iodinated compounds.

The preparation of liposomes containing opacifying contrast agents is disclosed in the following patents, herein incorporated by reference: U.S. Pat. No. 4,192,859, FR 2561101, U.S. Pat. No. 4,567,034, GB 134869, GB 2135268, GB 2135647, GB 2156345, GB 2157283, EP-A-179660, U.S. Pat. No. 4,192,859, U.S. Pat. No. 4,744,989, U.S. Pat. No. 4,830,858, U.S. Pat. No. 5,393,530, U.S. Pat. No. 5,702,722, U.S. Pat. No. 5,895,661, U.S. Pat. No. 5,980,937, U.S. Pat. No. 5,312,615, U.S. Pat. No. 5,445,810, U.S. Pat. No. 5,626,832.

As formerly said, the iodinated agents listed above are characterized by high water solubility, safety of use in vivo, pharmacological inertia, high chemical stability, low viscosity, low osmolarity and, advantageously, the capability of further providing effective magnetization transfer, in the presence of the radiofrequency signal applied at the absorption frequency of mobile protons.

Remarkably, moreover, said compounds have a low in vivo toxicity so that they can be safely used at high dosages in diagnostic contrastographic applications.

Scheme 5 shows some data (Merck Index $12^{th}$ ed.) concerning toxicity of Iopamidol, Iopromide, Metrizamide and Sodium Diatrizoate.

Scheme 5

Iopamidol

4943. LD50 in mice, rats, rabbits, dogs (g/kg): 44.5; 28.2; 19.6; 34.7

Iopromide

4948. LD50 in mice, rats (g iodine/kg body weight): 16.5; 11.4 i.v.

Metrizamide

6077. LD50 i.v. in mice: 15 g/kg (Torsten); 18.6 g/kg (Salvenson); 11.5 g/kg (Sovak); 17.3 g/kg (Aspelin).

Sodium diatrizoate

2975. LD50 i.v. in rats: 14.7 g/kg (Langecker).

Moreover, the chemical stability of said compounds is considered an important feature which makes possible their treatment in autoclave at high temperatures, during sterilization of pharmaceutical injectable forms.

As an example, pharmacokinetic and pharmacotoxicy of Iopamidol, a molecule characterized by three amido protons that exchange with water protons, have been the object of a number of clinical studies (see e.g. Radiologica Diagnostica, 7, 73-82, 1982; Diagnostic Radiology, 7, 83-86, 1982; Drug Research, 40, 7, 1990; Clin. Pharmacokinet., 32, 180-193, 1997).

Interestingly, Iopamidol (see Experimental Section) used in MRI saturation transfer, allows to reduce even to 80% the signal from water at a 2.1 T magnetic field.

The compounds of the invention can be used for enhancing the contrast of images produced in various radiographic and/or MRI procedures, including those concerning intravascular imaging such as myelography, urography, angiography (e.g. cerebral and peripheral angiography), cardiography (e.g. coronary arteriography and/or aortography), arthrography, for example of animal or human organs such as heart, breast, brain, knee, liver and central nervous system.

An interesting application of the MT-based MRI imaging method provided by the present invention is its the use in angiographic diagnostics of blood vessels in organ perfusion imaging.

Also interesting is the possibility of using the magnetization transfer MRI technique, which allows differentiation between blood vessels and the more vascularized tissues of an organ and those characteristic of parenchyma.

An equation for rationalizing MRI magnetization transfer was first formulated by Forsen and Hoffman in J. Chem. Physics, 1963, 39 (11), 2892-2901 and is reported in the following:

$$M_s/M_o \approx [1/(1+KT)] \quad (1)$$

wherein Ms is the value of the water proton signal during the saturation of the corresponding proton signal of the "exogen" molecule, Mo is the value of the signal without irradiation, i.e. in the presence of irradiation with the opposite frequency to that irradiated during the saturation phase, K is the exchange constant of mobile protons with water and T is the spin-lattice relaxation time of water protons (J. Magn. Res., 133, 36, 1998).

The Magnetization Transfer or, more precisely, the amount of saturation transfer (ST) registered in a MT based MRI procedure following irradiation of the mobile proton(s), is conveniently quantified as ST % according to the following equation (2)

$$ST\% = 100 \times (1 - M_s/M_0) \quad (2)$$

in which Ms and Mo have the former meanings.

The saturation transfer ST is affected by some parameters, such as intensity of the applied magnetic field, intensity of the radiofrequency field, chemical group involved in the prototropic exchange with water, pH, temperature of the medium, and water and "exogen" compound contents, i.e., in other words, its local concentration in the concerned tissue. Thus, for instance, an increase in the intensity of the radiofrequency field used for the saturation corresponds to an higher decrease of the bulk water signal. The value of the applied magnetic field is very important in that, for a given system, high $B_0$ values allows for higher exchange rates before incurring in a too large resonance broadening of exchangeable protons, which would make its efficient saturation with the irradiating field no longer possible.

Moreover, both pH and temperature affect the proton exchange rate; in particular, an increase in temperature always induces an increase in the exchange rate, while pH catalyzes the exchange as it deviates from neutrality. Around pH 7, the exchange rate of the mobile protons is, in general, minimum and it increases when the solution is acidified (pH<7) or alkalinized (pH>7).

Interestingly, when Iopamidol is used with the MT based procedure of the instant invention, a relevant ST effect is registered allowing a MT based contrast to be clearly detected at physiological pH and temperature, thus consenting its advantageous use in in vivo MRI imaging.

Experiments were conducted to compare the capabilities of the amino acids L-alanine, L-glutamine and L-lysine, GD-DTPA and the iodinated contrast agent iopamidol in MT imaging. In a first series, tests were conducted at physiological pH and temperature. A second series of tests were conducted at acidic pH. The results of both series are shown in Table 1 below:

TABLE 1

| Agent | Saturation Transfer Value pH = 7.4 | Saturation Transfer Value Acidic pH |
|---|---|---|
| L-alanine | 0 | 20 |
| L-glutamine | 0 | 50 |
| L-lysine | 0 | 30 |
| Gd-DTPA | 0 | <4 |
| Iopamidol | 68 | <4 |

In the first series of tests, Z-spectra and corresponding Saturation transfer (ST) profiles were measured at 7 T, pH 7.4 and 312 K, for aqueous solutions of iopamidol (30 mM), L-amino acids alanine, glutamine and lysine (each 30 mM), Gd-DTPA (1 mM) and Iopamidol (30 mM). Only in the case of Iopamidol was a relevant ST registered, allowing MT-based contrast under physiological conditions. Under physiological conditions, Gd-DTPA and the L-amino acids alanine, glutamine and lysine failed to provide any detectable signals The second series of tests were conducted at acidic pH, 312K and 7 T where as in the first series Z-spectra and corresponding Saturation transfer (ST) profiles were measured: L-alanine at pH=4, 30 mM; L-glutamine at pH=5.2, 30 mM; L-lysine at pH=4, 30 mM Gd-DTPA at pH=4, 1 mM; and Iopamidol at pH=4, 30 mM. The amino acids were able to provide contrast at acidic pH 4 (L-alanine and L-lysine) or 5.2 (L-glutamine) confirming that they are only useable outside of normal physiological conditions. Under acidic conditions, both Gd-DTPA and Iopamidol failed to provide MT contrast.

Consequently, as shown above, MT-based contrast is never possible with Gd-DTPA (a conventional MRI contrast agent), independent of the pH of the solution. Further, amino acids can not be used for in vivo imaging. Conversely, as shown above, Iopamidol does provide MT contrast at physiological pH and thus can be advantageously used in in vivo MT imaging as further discussed herein.

Since the temperature and pH affect, as said, the amount of saturation transfer and, therefore, the decrease in the recorded bulk water signal, the intensity of this latter may ultimately be held liable, or, in other words "responsive" for the above physiological parameters in the solution or in the body organ or tissue under examination.

It stems from the above that contrast agents endowed with at least one exchangeable proton whose saturation transfer capability correlates to a parameter of diagnostic interest or, in other words, is "responsive" for a parameter of diagnostic interest at physiological conditions, may by used in in vivo MT based procedures to provide diagnostic evaluation of the said parameter in a human or animal body organ, fluid or tissue.

Now we have interestingly proven that iodinated contrast agents according to the invention, having mobile protons (belonging to amino function(s)) able to exchange with bulk water, may advantageously be used in MT based procedures as "responsive" agents for the determination of parameters of diagnostic interest.

Accordingly, in a further embodiment thereof, the instant invention relates to the use of iodinated contrast agents having mobile protons able to exchange with bulk water as responsive agents for the determination of physiological parameters of diagnostic interest both in vivo and in vitro (ex vivo), by use of MT based MRI imaging technique.

Physiological parameters of interest according to the instant invention include, for instance, temperature and pH, the latter being particularly preferred.

Preferred agents for use as responsive agents according to the invention include iodinated agents endowed with two pools of mobile protons having exchange rate with surrounding water protons catalyzed by local temperature or, especially, by local pH.

Most preferably, the agent is Iopamidol.

Accordingly, in an especially preferred embodiment, the present invention relates to a method for the in vivo or in vitro (ex vivo) assessment of the physiological pH in a human or animal body organ, region, fluid or tissue by use of MT based MRI techniques, which comprises using Iopamidol as pH responsive agent.

Interestingly, Iopamidol, includes two pools of mobile amidic protons whose exchange rate with the surrounding water protons is differently catalyzed by the pH of the medium.

More particularly, Iopamidol possesses three exchangeable amidic proton pools, two of them having the same magnetic resonance frequency offset at 4.2 ppm, whereas the remaining has a chemical shift at 5.5 ppm, when setting at 0 ppm the water chemical shift. In addition, the exchange rate with water protons of the set of mobile amidic protons at 4.2 ppm is lower and differently catalyzed by the pH of the medium than that of the proton pools at 5.5 ppm, as clearly apparent in FIG. 4.

By consequence, a ratiometric approach, for instance provided by WO 00/66180 may be exploited, based on the Saturation Transfer effect arising from the two different amidic proton pools, that makes the measured saturation transfer ST independent on the absolute local concentration of the iodinated agent.

In greater details, when Iopamidol is used for the in vivo determination of the physiological pH according to an especially preferred aspect of the instant invention, a ratiometric approach may be exploited based on the following equation (3)

$$\frac{[(M_0 - M_s)/M_s]_{4.2ppm}}{[(M_0 - M_s)/M_s]_{5.5ppm}} \qquad (3)$$

in which the Saturation Transfer effect is measured as a ratio of the contribution arising from the two different amidic proton pools of Iopamidol, thus rendering the obtained measure independent on the absolute concentration of the administered agent, but only related to a relative concentration deriving from the ratio.

In the former equation [3], $M_s$ is, as said, the intensity of the water signal measured in the presence of an irradiating field RF at a given frequency offset, i.e. at the frequency of the exchanging proton pools (4.2 or 5.5 ppm), and $M_0$ is the value of the signal without irradiation, i.e. in the presence of irradiation with the opposite frequency to that irradiated during the saturation phase (−4.2 or −5.5 ppm).

It stems from the above that the method of the instant invention that comprise using Iopamidol as a responsive agent for the in vivo assessment of the physiological pH in a human or animal body organ, region, fluid or tissue, further preferably comprises calculating the ST effect by exploiting a ratiometric approach based on the former equation [3].

The known magnetization transfer techniques can be carried out coupled with different kind of sequences, such as those known as "gradient or field echo" and "spin echo and fast spin echo". However, the sequences currently used in imaging are "gradient or field echo" rather than "fast spin echo".

Now, to make practically feasible and effective the exploitation of an exogenous contrast agent (such as Iopamidol) in in vivo diagnostics it is necessary to front drawbacks, at least to some extent related to the use of the above sequences, that make still challenging the practical exploitation of CEST imaging in in vivo condition.

In particular, when a CEST contrast agent is used in vivo, major problems may arise from changes of its local concentration during the imaging acquisition time.

That is because, to correctly measure the saturation transfer effect promoted by the administered agent, it is necessary to collect a set of images covering the whole saturation frequency offsets or, in other words, to acquire a Z-spectrum (the whole set of images) covering a range of frequency offsets comprising the resonance offset(s) of the mobile proton(s) (of the administered agent) and the water chemical resonance.

Due to the long saturation time requested by a complete (steady-state) saturation of the whole mobile proton pools in the diamagnetic molecule, the total scan time for a standard MT study can take up to 30 minutes with formerly listed conventional spin-echo sequences (this is, in fact, the time needed to acquire the whole Z-spectrum, with the acquisition of 20-40 MRI images at different offsets, by using the above sequences).

It is a very long time from a clinical point of view, uncomfortable for a patient, in which, moreover, the local concentration of contrast agent is subject to continuous changes along the different points (frequency offsets) of the Z-spectrum. Therefore, beside being clinically impractical, a so poor temporal resolution is also ineffective.

When working in in vivo conditions, further problems may also arise from direct saturation (spillover) effects, from endogenous (not symmetric) conventional Magnetization Transfer (MT), and from inter-voxel differences in the water resonance frequency offset due, for instance, to tissue heterogeneity, non optimal sample shimming and tuning, radiation damping, magnetic fields B0 and B1 inhomogeneity and periodical or not-periodical movements and deformations due to organ motions. In addition, erroneous determination of the saturation transfer effect may also arise from noisy data, for instance due to scattered points in the Z-spectrum. All the above error sources may significantly limit the sensitivity and the accuracy of the MRI-CEST technique, for instance resulting in a fictitious increase or decrease of the measured values.

While a number of procedures are known for removing Magnetic B0 heterogeneity (see for instance, Contrast Media & Molecular Imaging, 3(4), 136-149, 2008), a need still exists of an improved MT based MRI procedures consenting to both increase the temporal resolution and to minimize all artifacts observed when working in in vivo conditions.

As a solution to the above need, a fast acquisition sequence scheme and an optimized post processing modalities have been prompted, herein provided, whose use in in vivo CEST based applications allow to significantly reduce the image acquisition time and to optimize the Signal to Noise Ratio in the recorded images. As a result, a more correct quantification of the Saturation Transfer effect is obtained resulting, in turn, in more accurate and reliable determinations of diagnostic parameters under investigation.

Accordingly, in a further embodiment, the invention relates to an improved fast sequence scheme allowing to increase the temporal resolution in MT based MRI procedures.

In the MRI field, a multiple echo acquisition scheme, otherwise known as Rapid Acquisition with Relaxation Enhancement (RARE) pulse sequence is known to greatly improve the temporal resolution, for instance, in conventional MRI to achieve T2 weighted images with faster scan times.

However; when this RARE acquisition scheme is used in MT techniques, beside promoting the desired reduction of the acquisition time, it also causes an unwanted reduction of the SNR (Signal to Noise Ratio) or CNR (Contrast to Noise Ratio), mainly due to the fact that the subsequent (more later) echoes have signal intensities lower than the first ones (as a general reference on RARE see, for instance, "MRI in practice, third edition" by Catherine Westbrook, Carolyn Kaut Roth and John Talbot, edited by Blackwell Publishing).

For contrast, an optimization of the Signal to Noise Ratio (SNR) or Contrast to Noise Ratio (CNR) is mandatory to ensure increased sensitivity and accuracy.

To overcome this drawback, we exploited an improved approach comprising using fast spin echo centric encoding sequences, instead of the linear ones conventionally used. According to this approach, the firstly recorded echoes, i.e. the echoes having the higher signal intensities, are placed in the central region of the k-space (the region encoding the contrast information), whereas the later echoes, having lower signal intensities, are placed in the outer region of the k-space (encoding the resolution information), Interestingly, when the said centric encoding sequence scheme is combined with a RARE factor equal to the matrix of phase encoding steps, for instance a 64×64 matrix as in the fast acquisition scheme herein provided, a significant improvement of the temporal resolution is obtained by further maintaining a good Signal to Noise Ratio, allowing reliable in vivo applications.

By contrast, a lower spatial resolution into recovered images could be observed that, in case, may be easily overcome through acquisition of a pre-contrast T2-weighted anatomical image, preferably acquired before the irradiation of the mobile proton pools with a suitable radiofrequency.

Figure 11:
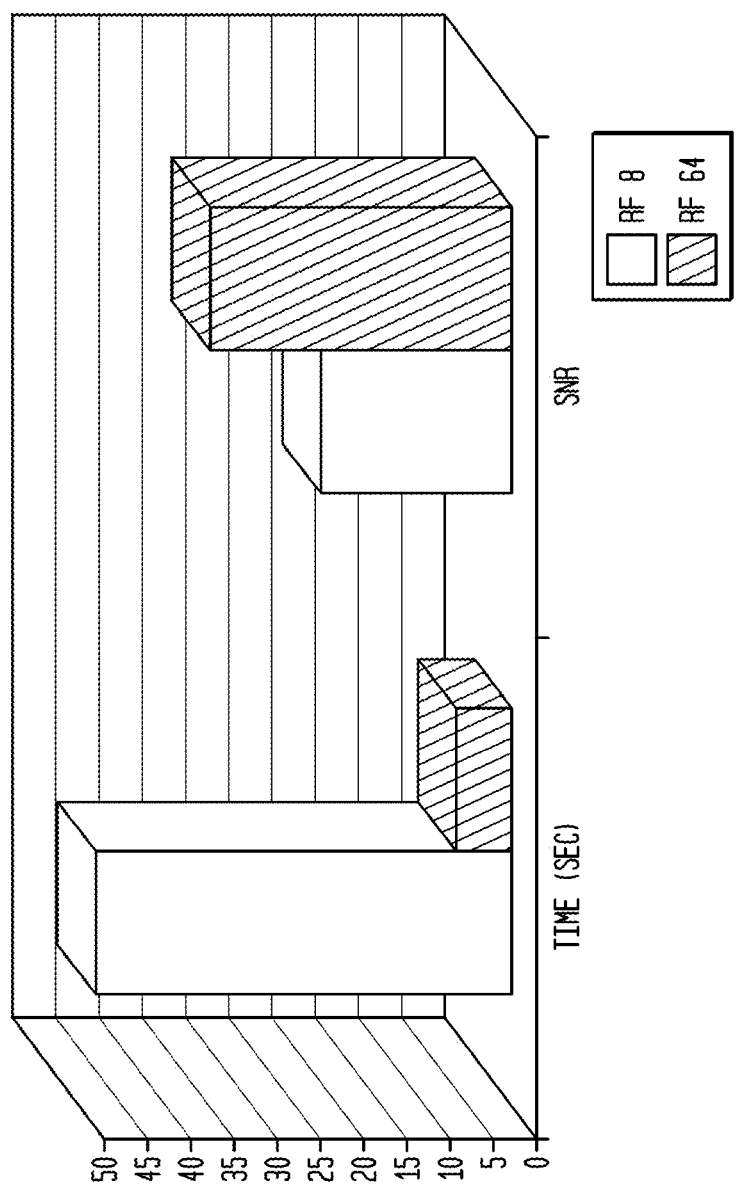
FIG. 11 compares the needed acquisition time and the signal-to-noise ratio (SNR) with conventional spin echo (Rare Factor=8, linear encoding, matrix size=64×64, TR=6000 see) and fast spin echo centric-encoding-based sequence schemes (Rare Factor=64, centric encoding, matrix size=64×64, TR=6000 sec) for a single ST image obtained in vivo irradiating at 4.2 ppm the kidney regions. The figure shows a net reduction of the requested acquisition time of a factor 8, exactly from 48 to 6 seconds.

The gain in resolution time provided by the use of the fast spin echo centric-encoding-based sequences of the invention results clearly from FIG. 11, in which the acquisition time and the SNR requested for fast spin echo with conventional linear encoding (RARE factor 8) and with centric encoding sequence schemes (RARE factor 64) are compared. The figure, in particular, shows that the acquisition time, for a single ST image, passes from 48 (with conventional) to 6 seconds (with centric-encoding sequences), corresponding to a whole imaging time of a few minutes, preferably less than 10 minutes and, more preferably, equal to or even less than 5 minutes.

It stems form the above that, in the method of the instant invention the imaging with Magnetization Transfer techniques is preferably carried out coupled with fast spin echo sequences or different, provided that fast, sequences. More preferably, the imaging with Magnetization Transfer techniques is carried out coupled with fast spin echo, centric-encoding-based sequences.

In an additional embodiment the instant invention relates to improved post processing modalities consenting to further increase the Signal to Noise Ratio (SNR) and to optimize the quantification of the Saturation Transfer effect observed in in vivo CEST imaging.

In greater details an improved modality is herein provided in which the analysis of the different images taken at different frequency offsets is performed on pixel-by-pixel basis, through interpolation of the Z-spectrum by smoothing splines. According to this modality the measure of the ability of the B-spline to pass through all the points of the Z-spectrum is expressed in term of chi-squared values (coefficient of determination or $R^2$), parameter reporting on the goodness of the interpolating curve to strictly follow all the experimental points. In particular, the interpolation of reliable, not noisy data gives rise to high $R^2$ values, while, conversely, in presence of noisy data the interpolating curve is not more able to pass through all the points of the Z-spectrum, thus resulting in decreased $R^2$ values (in this respect see, for instance, Draper, N. R. and Smith, H. (1998). Applied Regression Analysis. Wiley-Interscience). By exploiting this approach, combined with the use of a low regularization factor to reduce the flexibility and thus the ability of the B-spline to pass through all the Z-spectrum points, it is possible to discriminate between smooth, not-scattered data, and noisy or scattered data as a function of the $R^2$ value they provide.

By following this approach a post processing modality, hereinafter called "$R^2$ filter modality" has been then prompted, in which a filter is used that acts by removing (from the whole set of recorded images constituting the Z-spectrum) all pixels having low R2 values, thus avoiding that erroneous and/or fictitious contribution arising from noisy data can affect the measured ST effect.

As a result, a significant increase of the goodness of the recovered ST effect is obtained, in turn resulting in an increased sensitivity of CEST method and in more reliable diagnostic evaluations.

A further improvement of the validity of the calculated ST may also be obtained by exploiting a different post-processing procedure, herein provided, that is based on the exploitation of the B-splines properties.

In greater details we have seen that an enhancement of the calculated ST effect is obtained when the interpolation of the Z-spectrum is performed with an asymmetric B-spline. More particularly, according to this modality, the Z-spectrum in the negative frequency offset, where it is expected to have no ST effect from the exogenous contrast agent, is fitted with a low regularization factor i.e. with a more rigid interpolating curve, thus reducing the influence of noisy data through the R2 filter. Instead, the spectrum in the positive frequency offset is interpolated with a high regularization factor in order to increase the sensitivity toward small ST effect arising from the mobile proton pools.

This post processing modality, hereinafter called "asymmetric enhancing modality" or "asymmetric interpolation modality" (as used herein interchangeably) is novel and constitute a further object of the instant invention as well as a MT based MRI method including its use.

Figure 12:
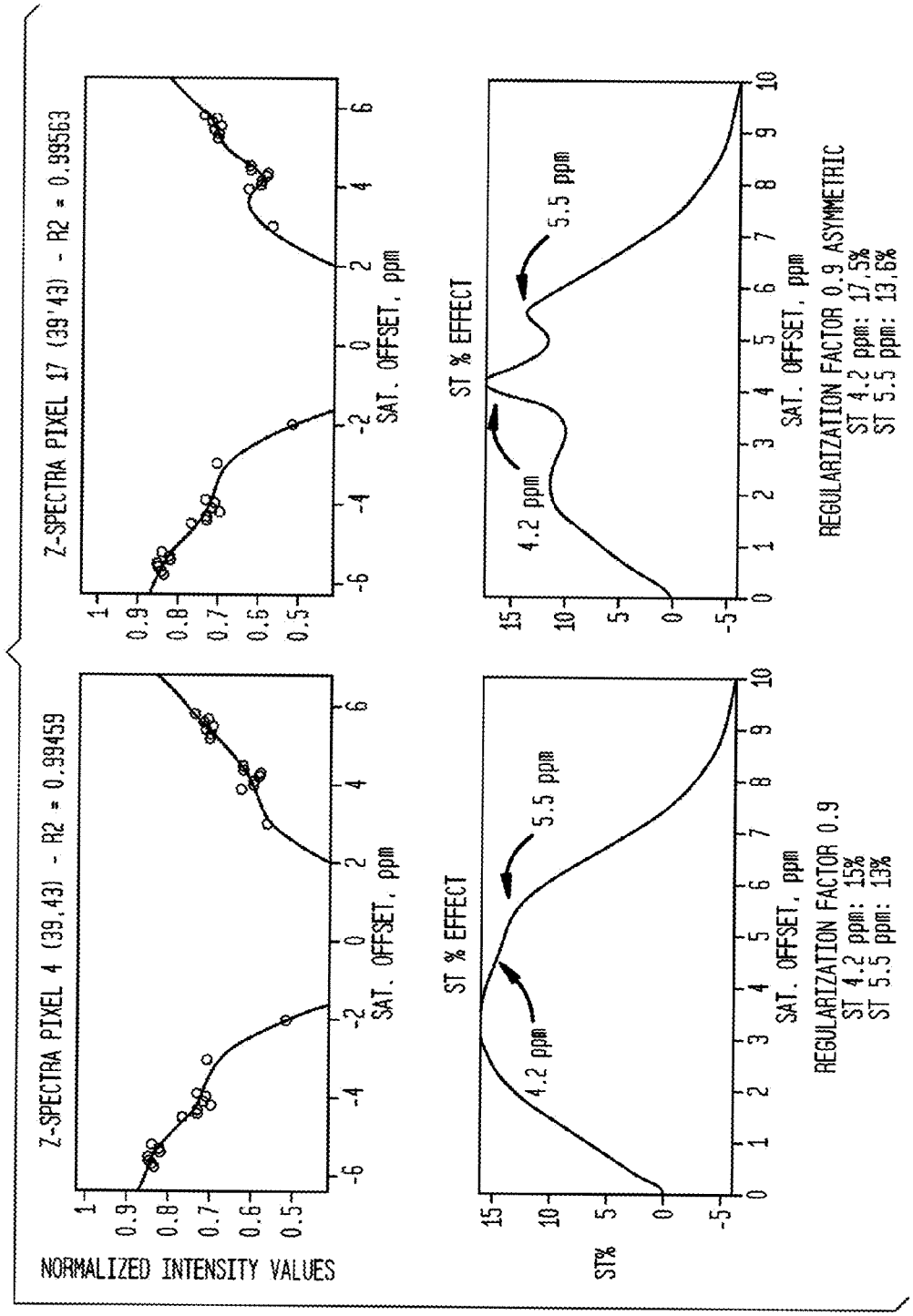
FIG. 12 compares the ST effect measured at 4.2 and 5.5 ppm with conventional symmetric interpolating smoothing-spline (left) and corresponding ST effect obtained with asymmetric analysis (right). The figure reports the gain on ST obtained with asymmetric analysis for both the frequency offset and the improved depiction of the two peaks.

The improvement obtained on the calculated ST by using the modality is clearly apparent from FIG. 12, in which ST % calculated with symmetric and asymmetric interpolation are compared, showing that the calculated ST value (at 4.2 ppm frequency offset) passes from 15% (symmetric) to 17.5% by using the asymmetric modality herein provided.

It is clear to a skilled in the art that former fast spin echo centric-encoding-based sequence scheme and the improved "R2 filter" and "asymmetric interpolation" modalities, which constitute embodiments of the invention, may advantageously be exploited in all in vivo CEST based MRI imaging methods, independently on the administered CEST agent as well as, especially, in CEST based MRI imaging methods for the in vivo assessment of a physical-chemical parameter of diagnostic interest to provide increased temporal resolution as well as improved sensitivity and more reliable and accurate diagnostic evaluations.

Moreover, it is clear that, in each CEST-based MRI imaging method, including, for instance, the method provided by the invention and using radiographic contrast agents for obtaining in vivo or in vitro, (ex vivo), images, each of the above fast spin echo centric encoding sequence scheme, R2 filter and asymmetric enhancing post processing modalities can be exploited optionally, and independently of each other, preferably combined with a ratiometric approach based on equation (3) to provide a ratiometric Saturation Transfer effect that is independent on the local agent concentration.

In a preferred embodiment of the invention the herein provided single-shot centric encoding sequence scheme and improved post processing modality(es) are used in a CEST based MRI method for the in vivo assessment of the physiological pH in a human or animal body organ, region, fluid or tissue by use of MT based MRI techniques in which Iopamidol is used as pH responsive agent. More preferably, the said method further comprises exploiting a ratiometric approach for calculating a ratiometric saturation transfer effect and, in turn, a pH map which is independent on the local agent concentration.

In greater details, in a preferred embodiment thereof, the instant invention relates to a method for in vivo mapping the physiological pH in a human or animal body organ, region, fluid or tissue by use of CEST based MRI techniques which includes administering a diagnostic formulation comprising Iopamidol as contrast agent to an individual or to an organ or other body part or tissue of the individual, irradiating the (Iopamidol) mobile protons with a radiofrequency field tuned on thereof resonance frequency, collecting a Z-spectrum, preferably by exploiting a single-shot fast spin echo centric-encoding-based sequence scheme, optionally optimizing the obtained spectrum, on a pixel by pixel bases, through correcting for B0 inhomogeneity and removing noisy data by using a "R2 filter" modality, calculating the Saturation Transfer effect, preferably through interpolation of the Z-spectrum by smoothing splines, by means of the asymmetric enhancing modality, and, in turn, the pH values, preferably through exploiting a ratiometric approach based on Equation 3 and by using a suitable conversion curve. Optionally, the pH map obtained with the above method is superimposed on an anatomical image recorded before collecting the Z-spectrum.

More particularly, in an especially preferred embodiment, the invention relates to a method for in vivo or in vitro (ex vivo) mapping of the physiological pH in a human or animal body organ, region, fluid or tissue by use of CEST based MRI techniques that comprises:

(a) administering a diagnostic formulation comprising Iopamidol as contrast agent to an individual or to an organ or other body region, fluid or tissue of the individual, (b) irradiating Iopamidol mobile protons with a radiofrequency field tuned on thereof resonance frequency thus inducing, through chemical exchange, saturation transfer to the bulk water signal, and, optionally recording the anatomical image of the body organ, region, fluid or tissue of interest, (c) collecting the Z-spectrum, (d) calculating the ST effect, (e) calculating, from obtained ST, the map of the physiological pH and, optionally, superimposing the obtained pH map to the recorded anatomical MR image.

In the said method the spectrum Z is preferably collected by use of a single-shot fast spin echo centric-encoding-based sequence scheme and, then, optimized through correction, pixel-by-pixel, of $B_0$ inhomogeneities and removal of noisy data by use of a R2 filter modality.

Moreover, the step (d) of the method preferably comprises calculating the Saturation Transfer effect at all the experimental point of each frequency offset through an asymmetric interpolation of the Z spectrum by smoothing splines, and then calculating the corresponding ratiometric ST effect values through exploiting the ratiometric approach of equation (3).

From obtained ratiometric ST values the pH map is then obtained, preferably by using a calibration curve, for instance as detailed in the following.

Exemplary application of the preferred embodiments of the invention method are comprised in the experimental section below.

Figure 7:
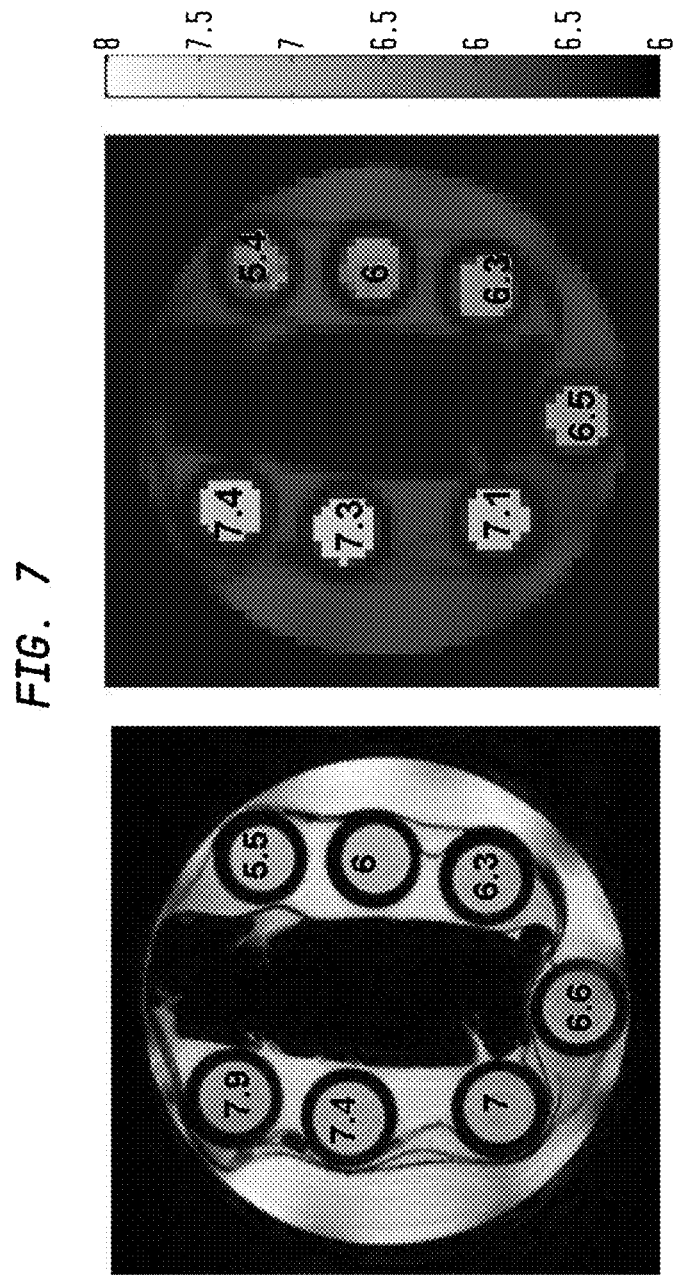
FIG. 7 relates to in vitro tests and reports pH values, calculated, by using the ratiometric method, from a phantom containing seven vials of a 30 mM Iopamidol phosphate-buffer solution titrated in the pH range from 5.5 to 7.9, with an irradiation power pulse of 3 µT.

For instance, pH values obtained in vitro from a phantom comprising seven vials of a 30 mM Iopamidol phosphate-buffered solution are shown in FIG. 7.

Figure 6:
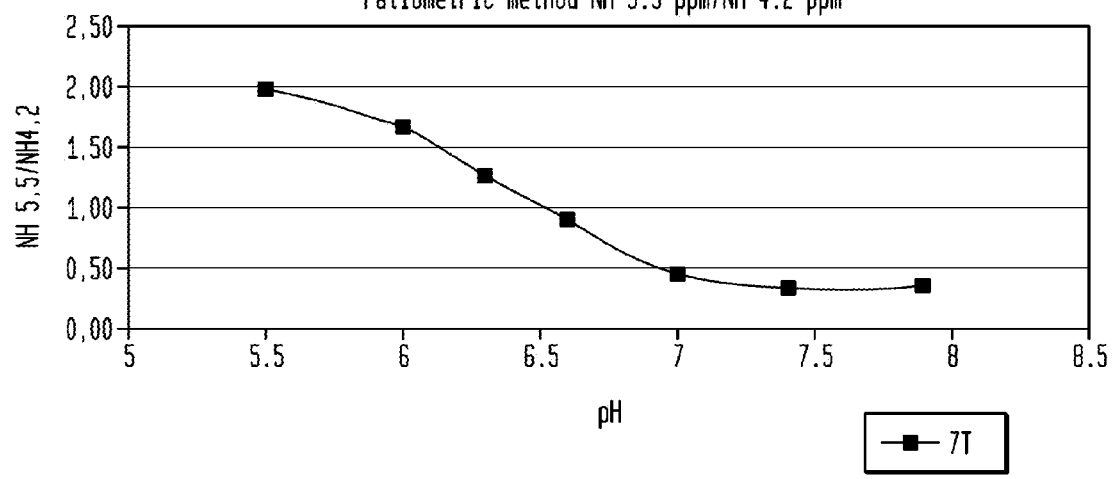
FIG. 6 shows the dependence of ST effect from pH (calibration curve) that results by applying the ratiometric method to the saturation transfer effect arising from the two different Iopamidol amidic proton pools at 4.2 and at 5.5 ppm, at different pH and by using irradiation power pulses of 3 µT and 6 µT, respectively.

A calibration curve useful to convert a given ratiometric ST, for instance deriving from in vivo pH mapping according to the invention, into the corresponding pH value is shown in FIG. 6.

Figure 10:
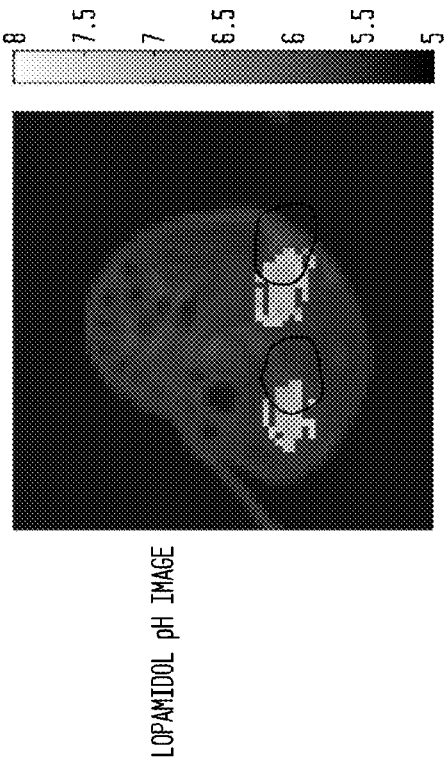
FIG. 10 shows the pH map calculated by using the ratiometric method from the ST map of FIG. 9. The pH map is superimposed on the corresponding anatomical image.

A pH map obtained in a mouse administered with 50 μL of Iopamidol solution (370 mgI$_2$/mL) is, moreover, shown in FIG. 10.

In the methods provided by the invention the iodinated contrast agents are used at concentrations which vary depending on the compound used and the particular diagnostic use.

As a rule, the examination of a specific district of the human body determines the amount and the corresponding concentration used.

The pharmaceutical formulation of the contrast agent, which is usually an aqueous solution, contains for example 15 g of compound per 100 mL of solution, corresponding to a iodine amount ranging from 50 to 500 mg per mL. However, solutions containing lower amounts of the contrast agent can also be used.

The amount of solution used in the investigations carried out according to the invention is usually comparable to that used in radiological analysis and varies depending on the concerned body site: for example, 5 to 15 mL in myelography, 3 to 5 mL in radiculography and 1 to 2 mL in ventriculography. The solution or suspension containing the contrast agent can optionally be administered directly through the enteral route. For example, solutions or suspensions containing 1 to 100 mmoles of contrast agent, suspended in 1-2 l of physiologically compatible solution, can be used.

The compounds of formula (I), (II), (III) and (IV) can be administered by the oral or enteral route.

For the parenteral administration, they are preferably formulated as sterile aqueous solutions or suspensions, with pH ranging from 6.0 to 8.5.

Said aqueous solutions or suspensions can be administered in concentrations ranging from 0.02 to 500 mM.

These formulations can be lyophilized and supplied as such, to be reconstituted just before the use. For the gastrointestinal use or for injection to body cavities, these agents can be formulated as a solution or suspension containing suitable additives in order to, for example, control viscosity, such as stabilizers, agents for controlling dissolution, anticoagulants, excipients used in the preparation of formulations and water soluble, physiologically compatible mineral salts.

The following examples illustrate the invention in greater detail.

Example 1

Effect of pH on 50 mM Iopamidol Solutions

The exchange rate between amido protons and water is affected by the pH of the solution. When measurements are carried out at 2.1 T magnetic field and at a temperature of 39° C., the transfer effect is maximum at pH 7.5. This effect decreases as pH becomes both more acid and more basic.

The effect on the decrease of the water signal in the corresponding magnetic resonance imaging, is anticipated by the measurements of R2 (=1/T2) of water protons as a function of the solution pH.

In Table relaxation rate R2 values (=1/T2) of water protons in a 50 mM Iopamidol solution as a function of pH at 2.1 and 9.34 T. Measurements were carried out with a JEOL EX-400 spectrometer at 25° C. using the CPMG sequence for the determination of T2.

TABLE

| | PH | | | | | | | | | | |
|---|---|---|---|---|---|---|---|---|---|---|---|
| | 3.3 | 4.7 | 5 | 5.6 | 6.3 | 6.8 | 7.3 | 8.0 | 8.55 | 9.24 | 10.5 |
| R2 2.1T (s−1) | 0.46 | 0.60 | 0.62 | 0.64 | 1.10 | 1.64 | 1.93 | 1.12 | 0.54 | 0.39 | 0.30 |
| R2 9.34T (s−1) | 30.8 | 32.3 | 31.3 | 32.0 | 30.0 | 32.8 | 40.1 | 41.7 | 35.3 | 32.4 | 34 |

Example 2

Effect of the Temperature on a 200 mM Iopamidol Solution

A 200 mM Iopamidol solution at pH=6.74 was investigated at 2.1 T magnetic field intensity (JEOL EX-90 spectrometer). After irradiating the amido proton signal at 9.4 ppm, with attenuation of 300 dB, the area under the water signal was measured. Considering 100 the area of the water signal with irradiation at −9.4 ppm, a drastic reduction is observed following irradiation of the amido protons. The effect increases as temperature increase so that:

| | 15° C. | 25° C. | 39° C. |
|---|---|---|---|
| % residual signal | 39 | 30 | 24 |

Example 3

Effect of Radiofrequency Field Intensity on a 200 Mm Iopamidol Solution

A 200 Mm Iopamidol solution at pH=6.29 was investigated at 2.1 T magnetic field intensity and at a temperature of 39° C. (JEOL EX-90 spectrometer).

Considering 100 the area of the water signal with irradiation at −9.4 ppm, its decrease (expressed as % residual signal) was evaluated in the presence of a rf field tuned at 9.4 ppm (signal of the amido protons).

A 40% residual signal value is measured when the irradiating field has an attenuation of 400 dB, which decreases to 15% when the attenuation is 300 dB.

Example 4

Evaluation of the CEST Contrast Ability of 50 mM Iopamidol

Imaging of a 50 mM Iopamidol aqueous solution recorded with an MRI Bruker Pharmascan tomographer operating at 7.03 T. The sample is a plastic cylinder containing distilled water and a coaxial cone filled with the Iopamidol aqueous solution at pH 7.4.

Measurements were carried out at a temperature of about 21° C. using a spin echo sequence coupled with the saturation transfer technique.

The results are shown in FIG. 1.

The main parameters used in said sequence are listed in the following:
matrix 256×128
FOV 3.5 cm
slice thickness 2 mm
repetition time 4 s
echo time 18.3 ms
MTC power level 9 µT
n° of MTC pulses 380 with 104 µs pulse length (pulse shape=gauss).

The top left image was recorded applying the presaturation impulse at the amido protons resonance frequency (i.e. at 1280 Hz from water), the top right image was recorded applying the presaturation impulse at the frequency opposite to that of amido protons relative to bulk water (−1280 Hz), the bottom left image was obtained from the difference between the two first images, whereas the bottom right image was obtained without using the magnetization transfer technique.

Example 5

Evaluation of the CEST Contrast Ability of 25 mM Iopamidol

Figure 2:
FIG. 2 reports images obtained in contrast ability tests with 25 mM Iopamidol.

The procedures of Example 4 were followed, but using a 25 mM Iopamidol aqueous solution.
The results are shown in FIG. 2.

Example 6

Evaluation of the CEST Contrast Ability of 10 mM Iopamidol

Figure 3:
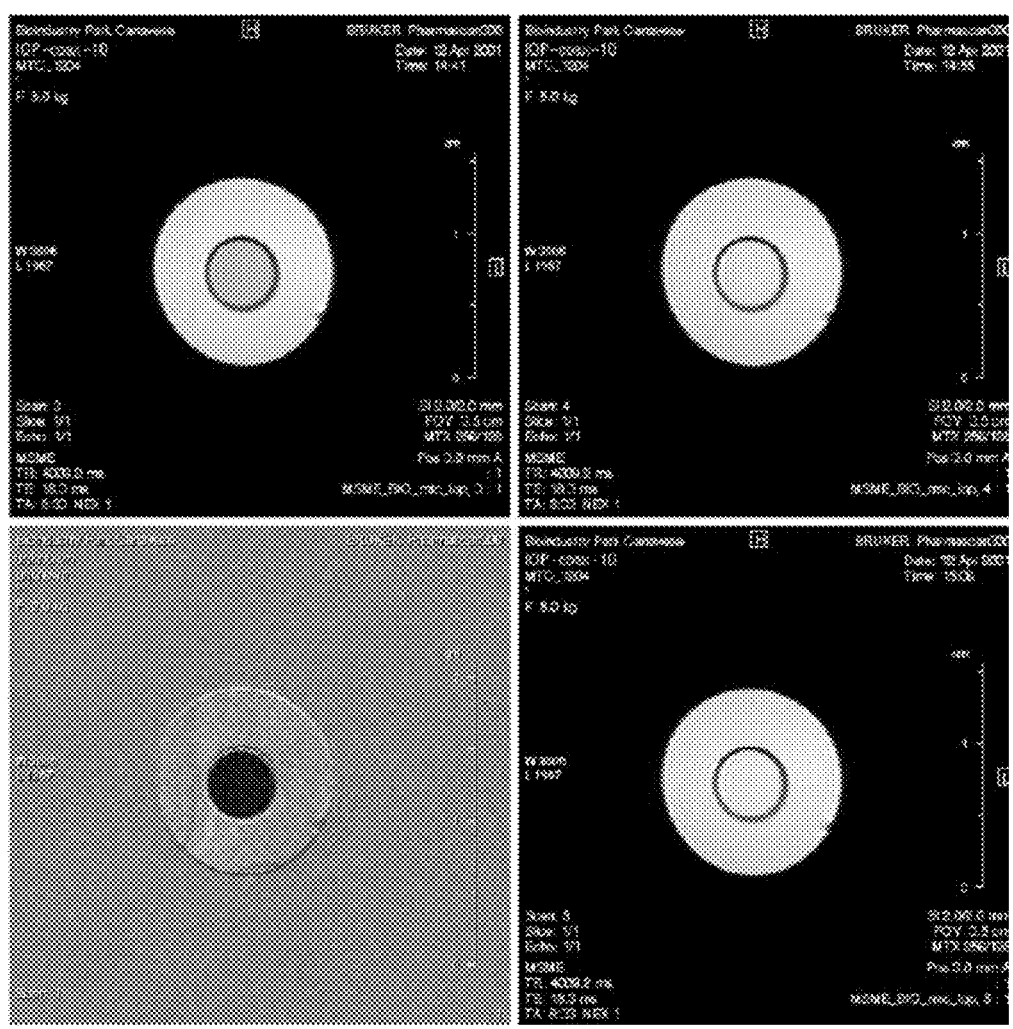
FIG. 3 reports images obtained in contrast ability tests with 10 mM Iopamidol.

The procedures of Example 4 were followed, but using a 10 mM Iopamidol aqueous solution.
The results are shown in FIG. 3.

Example 7

Evaluation of Chemical Exchange Rate of Iopamidol Amidic Protons at 4.2 and 5.5 ppm as a Function of pH

Figure 4:
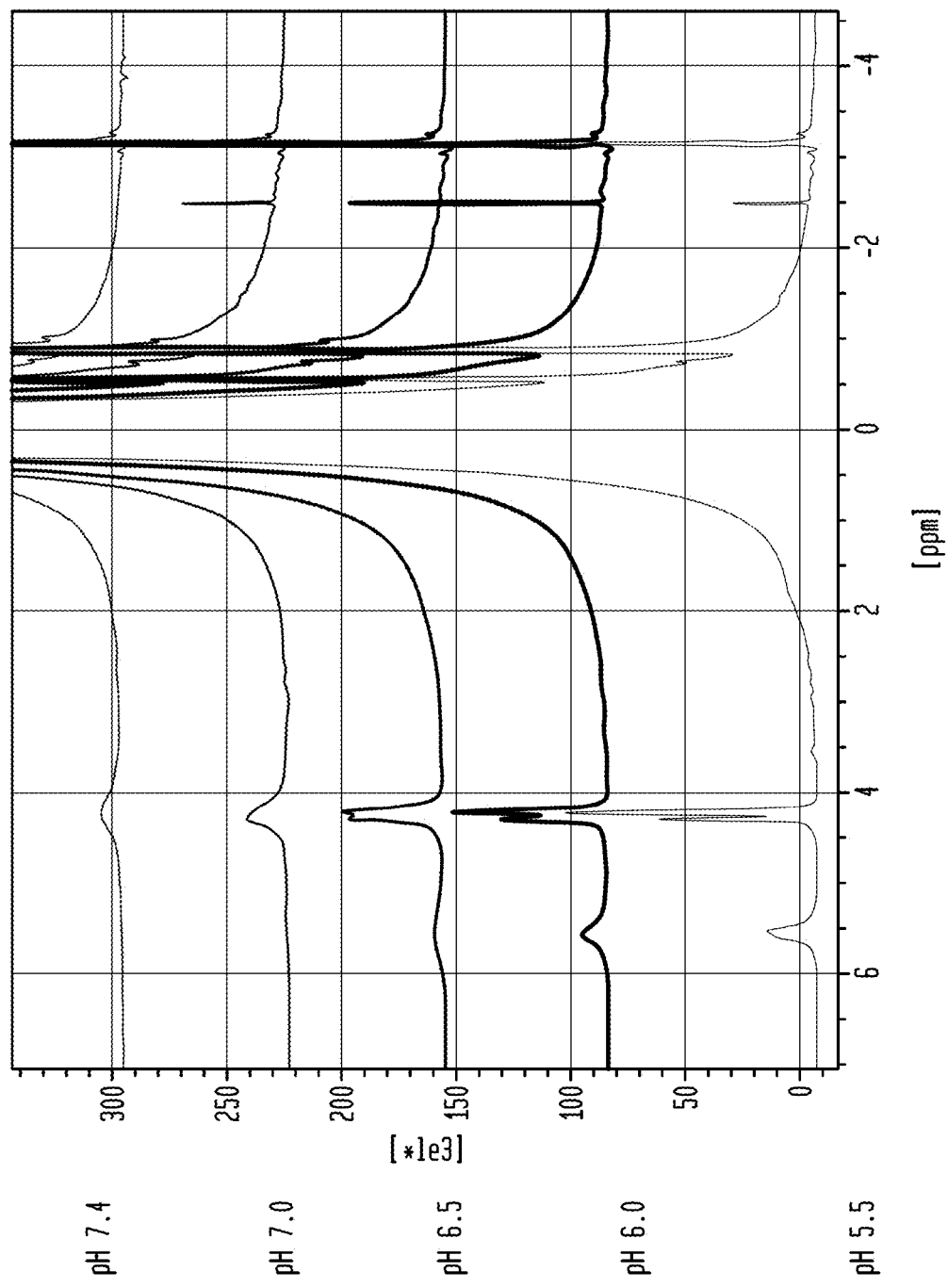
FIG. 4 shows the pH dependence of the chemical exchange rate of the two different amidic proton pools of Iopamidol, respectively at 4.2 and at 5.5 ppm.

NMR spectra were recorded on a Bruker Avarice 600 NMR spectrometer equipped with a variable-temperature probe heated at 308 K.
Regular 1D 1H NMR spectra (65 kHz spectral width, 256 k complex data points, $\pi/2=10$ μs, TR=s, 64 averages) were measured.
Samples were prepared by dissolving the appropriate amount of Iopamidol (200 mM) in aqueous phosphate buffer solution (10 mM). Five capillaries were prepared in the pH range 5.5-7.4. The pH value of the solutions was adjusted by adding small aliquots of either NaOH or HCl stock solutions. To enable frequency locking, a coaxial glass capillary insert filled with $D_2O$ was used. All spectra were calibrated relative to the $H_2O$ frequency. The results are shown in FIG. 4.

Example 8

Figure 5:
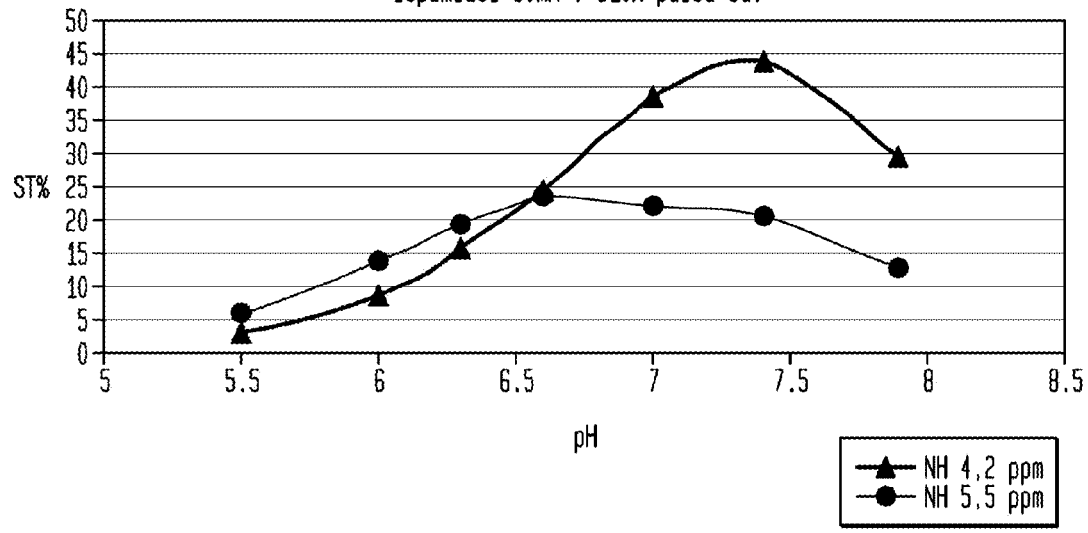
FIG. 5 reports the variation of the ST effects generated by the two proton pools of Iopamidol by changing pH. Used irradiation power pulse: 3 µT.

In vitro tests aimed to measure the variation of the ST effect generated by the two different proton pools of Iopamidol by changing pH.
The Imaging tests were performed by using a 30 mM Iopamidol phosphate buffer (0.010 M) solution. The imaging was recorded with an MRI Bruker Avance 300 tomographer operating at 7.03 T. The sample used was a plastic cylinder containing 7 plastic vials filled with the Iopamidol buffered solution trited in the pH range 5.5-7.9.
The determinations were carried out at a temperature of about 37° C. using a RARE spin echo sequence coupled with the saturation transfer technique.
The results are shown in FIG. 5.
The main parameters used in said sequence are listed in the following:
matrix 64×64
FOV 3.0 cm
slice thickness 2 mm
repetition time 5 s
echo time 14.88 ms
Rare Factor 8
NEX 2
MTC power level 3 μT, MTC duration 5 seconds, pulse shape=block pulse
The image was recorded applying the irradiation pulse in the range between −10 and 10 ppm with steps of 0.1 ppm.
ST effects were calculated according to equation 2.
The results are shown in FIG. 5.
The ratiometric approach of equation 3 is then exploited to calculate ratiometric ST values as a function of the pH thus obtaining a calibration curve, shown in FIG. 6, useful to convert a given ratiometric ST, for instance deriving from in vivo pH mapping according to the invention, into the corresponding pH value.

Example 9

Figure 8:
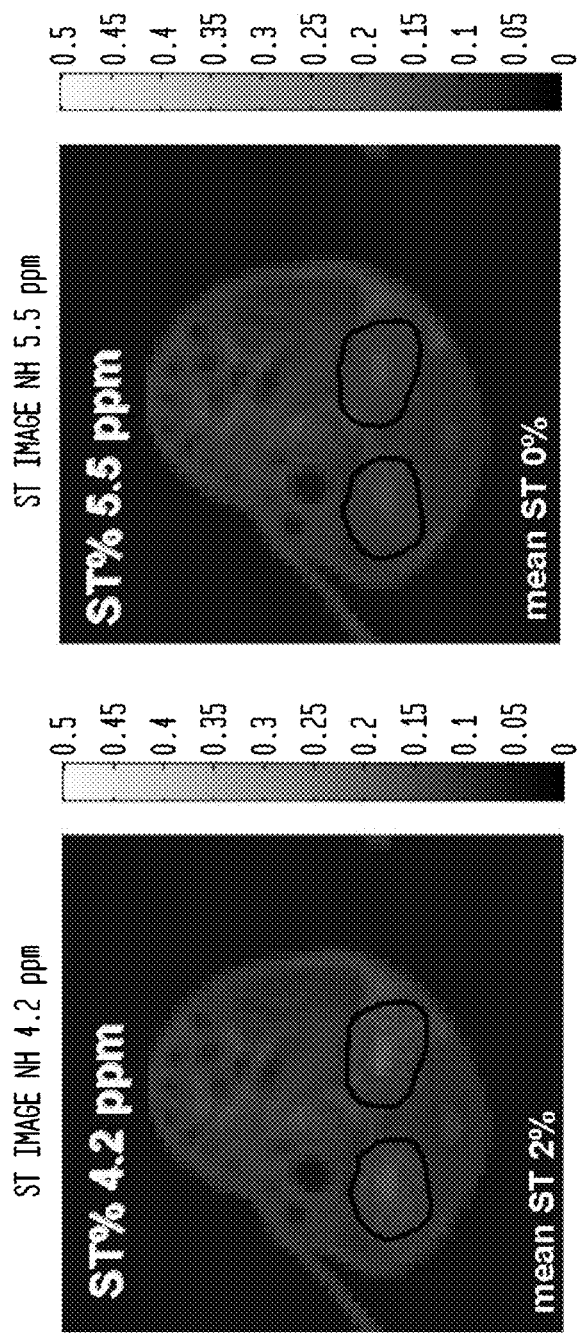
FIG. 8 reports cross-sectional images of a mouse obtained in in vivo tests. More particularly the Figure shows the ST effect calculated at 4.2 ppm and at 5.5 ppm in pre-contrast images. Obtained ST effect map is superimposed on the anatomical image in which the kidneys zone is circled.
Figure 9:
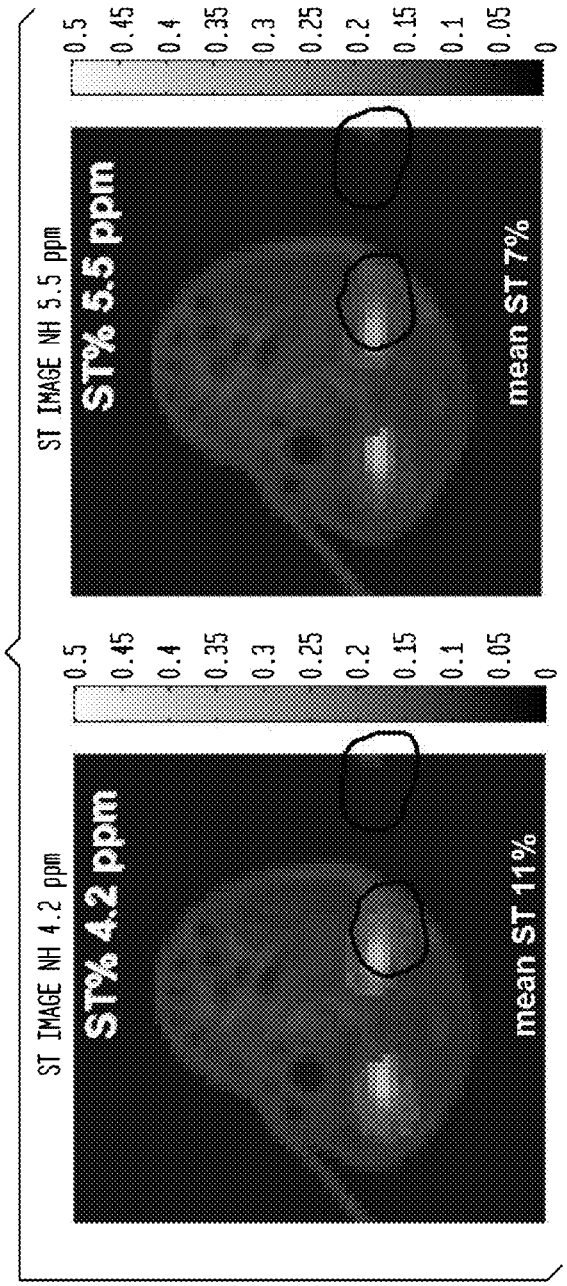
FIG. 9 reports the ST effect calculated at 4.2 ppm and at 5.5 pp in post-contrast images recorded on a mouse injected with 50 uL of a Iopamidol solution (solution concentration 370 mgI$_2$/mL, corresponding to a 0.7 mg I/g body weight). Obtained ST effect map is superimposed on the anatomical image in which the kidneys zone is circled.

In vivo tests. Determination of Saturation Transfer effect before and after injection of Iopamidol
MR images were acquired on a Bruker Avance 300 spectrometer operating at 7 T and equipped with a microimaging probe (Bruker Bio-Spin, Milan, Italy). SCID mice weighing 20-25 g were imaged using a 30 mm coil. Mice were anesthetized by a mixture of Rompum and Zoletyl intracoutaneously injected. Breath rate was monitored during all in vivo MRI experiment using a respiratory probe. 100 μL of a 500 mM solution of Iopamidol, corresponding to 0.75 mg I/g body weight was slowly injected via catheter into the tail vein.
Pre-contrast T2-weighted, RARE spin-echo images useful as anatomical reference was obtained with the following parameters: (TR/TE/R are Factor/NEX=5.0 s/4.5 ms/16/2), FOV=3 cm, matrix=256×256, slice thickness=2 mm).
Z-spectra were acquired in the frequency offset range ±10 ppm using a single-shot spin echo RARE sequence with centric encoding (typical setting TR/TE/NEXIRARE factor=6.0 s/4.14 ms/1/64) preceded by a saturation transfer pulse at 3 μT for 5 s and by a fat-suppression module. A 64×64 acquisition matrix was used with a slice thickness=2 mm and square FOV=3×3 cm. A total of 43 images were acquired, for the pre-contrast Z-spectum, with a total acquisition time of 4 min 18 sec.
After the acquisition of the Z-spectrum, Iopamidol was injected via catheter.
The post-contrast Z-spectrum was then acquired by using the same parameter used (and formerly reported) for the pre-contrast image.
The pre-contrast and post-contrast Z-spectrum images were interpolated with smoothing-spline and noisy pixel were removed by using the R2 filter modality.
Saturation transfer effects were calculated at each frequency offset, after interpolating the Z-spectrum with smoothing spline with a regularization factor of 0.9. The resulting ST effects for the two peaks at 4.2 and at 5.5 ppm were superimposed on the anatomical reference image. Obtained results are reported in FIG. 8 (pre-contrast) and FIG. 9 (post-contrast), respectively. A post-contrast pH map was then calculated by applying the ratiometric method of equation 3 to the post-contrast images of FIG. 9. More particularly, pixel by pixel the ratio of the ST effects measured, respectively, at 4.2 and 5.5 ppm is converted in the corresponding pH value by using the conversion curve of FIG. 6. A pH map is thus obtained and superimposed on anatomical images formerly obtained, shown in FIG. 10.

The invention claimed is:
1. A method for assessing the physiological pH, in a human or animal, by use of a chemical exchange dependent saturation transfer (CEST) based magnetic resonance imaging (MRI) technique, the method comprising the steps of:
(a) administering a diagnostic formulation comprising Iopamidol to an individual or to an organ or other body region, fluid or tissue of the human or animal,
(b) irradiating Iopamidol mobile protons to induce through chemical exchange, saturation transfer to the bulk water signal,
(c) collecting the Z-spectrum,
(d) obtaining the Saturation Transfer effects for each frequency offset through an asymmetric interpolation of the Z-spectrum by asymmetric smoothing splines, wherein a negative frequency offset is fitted with a low regularization factor and a positive frequency offset is fitted with a high regularization factor, and wherein the Z-spectrum is collected using fast spin echo centric encoding sequences, and (e) obtaining from the Saturation Transfer effects, a map of the physiological pH.

2. The method of claim 1 further comprising optimizing the collected Z spectrum through correction, pixel-by-pixel, of $B_0$ inhomogeneities and removal of noisy data by use of a $R_2$ filter modality.

3. The method of any one of claims 1, and 2 further comprising calculating a ratiometric ST effect.

4. The method of claim 3 comprising calculating the map of the physiological pH by using the calculated ratiometric ST values.

5. The method of claim 4 further comprising recording an anatomical image of the individual body organ, region, fluid or tissue of interest.

6. The method of claim 5 further comprising superimposing the obtained pH map on the recorded anatomical image.

* * * * *